US009292919B2

(12) United States Patent
Ando et al.

(10) Patent No.: US 9,292,919 B2
(45) Date of Patent: Mar. 22, 2016

(54) MEDICAL IMAGE DIAGNOSIS APPARATUS, MEDICAL IMAGE PROCESSING APPARATUS, AND MEDICAL IMAGE PROCESSING METHOD

(71) Applicants: Kabushiki Kaisha Toshiba, Minato-ku (JP); Toshiba Medical Systems Corporation, Otawara-shi (JP)

(72) Inventors: Kouji Ando, Tochigi (JP); Tatsuru Kurosaki, Tochigi (JP); Yasunori Ooshima, Tochigi (JP); Nobuhide Ol, Tochigi (JP); Takashi Koyakumaru, Tochigi (JP); Mitsuo Akiyama, Tochigi (JP)

(73) Assignees: Kabushiki Kaisha Toshiba, Minato-ku (JP); Toshiba Medical Systems Corporation, Otawara-shi (JP)

( * ) Notice: Subject to any disclaimer, the term of this patent is extended or adjusted under 35 U.S.C. 154(b) by 4 days.

(21) Appl. No.: 14/222,089

(22) Filed: Mar. 21, 2014

(65) Prior Publication Data
US 2014/0205164 A1 Jul. 24, 2014

Related U.S. Application Data

(63) Continuation-in-part of application No. PCT/JP2013/006944, filed on Nov. 26, 2013.

(30) Foreign Application Priority Data

Nov. 27, 2012 (JP) .................................. 2012-258852

(51) Int. Cl.
*G06K 9/00* (2006.01)
*G06T 7/00* (2006.01)
(Continued)

(52) U.S. Cl.
CPC .............. *G06T 7/0012* (2013.01); *A61B 8/5215* (2013.01); *A61B 8/461* (2013.01); *A61B 8/463* (2013.01)

(58) Field of Classification Search
CPC .......... A61B 8/463; A61B 5/055; A61B 6/03; A61B 5/00; A61B 8/461; A61B 8/5215; G06T 7/0012
See application file for complete search history.

(56) References Cited

U.S. PATENT DOCUMENTS 5,576,849 A * 11/1996 Murakami et al. ............. 358/2.1
8,979,741 B2 * 3/2015 Igarashi et al. ............... 600/160
(Continued)

FOREIGN PATENT DOCUMENTS

CN 1839761 A 10/2006
CN 1920854 A 2/2007
(Continued)

OTHER PUBLICATIONS

International Search Report mailed Dec. 24, 2013 for PCT/JP2013/006944 filed Nov. 26, 2013 with English Translation of Categories.
(Continued)

*Primary Examiner* — Shefali Goradia
(74) *Attorney, Agent, or Firm* — Oblon, McClelland, Maier & Neustadt, L.L.P.

(57) ABSTRACT

A medical image diagnosis apparatus of an embodiment includes: an image generation unit configured to generate a first image which is an original image, from a medical image taken by a medical imaging unit; an image conversion unit configured to process the first image to output a second image where a color tone of a predetermined region in the first image is kept and a color tone of a region other than the predetermined region is converted; and an image output unit configured to supply the second image to an output apparatus.

12 Claims, 8 Drawing Sheets

(51) Int. Cl.
  *A61B 8/08* (2006.01)
  *A61B 8/00* (2006.01)

(56) References Cited

U.S. PATENT DOCUMENTS

| 2009/0036741 | A1* | 2/2009 | Igarashi et al. | 600/160 |
| 2011/0229022 | A1* | 9/2011 | Yamada | 382/162 |

FOREIGN PATENT DOCUMENTS

| JP | 61-147293 A | 7/1986 |
| JP | 06-285065 A | 10/1994 |
| JP | 2001-154653 A | 6/2001 |
| JP | 2004-106196 A | 4/2004 |
| JP | 2006-136587 A | 6/2006 |
| JP | 2009-070075 A | 4/2009 |
| JP | 2012-221365 A | 11/2012 |
| WO | WO 2008/087886 A1 | 7/2008 |
| WO | WO 2009/104459 A1 | 8/2009 |

OTHER PUBLICATIONS

International Written Opinion mailed Dec. 24, 2013 for PCT/JP2013/006944 filed Nov. 26, 2013.
Ultrasound System LOGIQ E9.
Combined Chinese Office Action and Search Report issued Aug. 11, 2015 in Patent Application No. 201380003230.7 (with partial English language translation).

* cited by examiner

MEDICAL IMAGE DIAGNOSIS APPARATUS, MEDICAL IMAGE PROCESSING APPARATUS, AND MEDICAL IMAGE PROCESSING METHOD

CROSS-REFERENCE TO RELATED APPLICATION

This application is a continuation-in-part of International Application No. PCT/JP2013/006994, filed on Nov. 26, 2013, which is based upon and claims the benefit of priority from the prior Japanese Patent application No. 2012-258852, filed on Nov. 27, 2012, the entire contents of which are incorporated herein by reference.

FIELD

Embodiments described herein relate to a medical image diagnosis apparatus that can paste an image in a report or the like and display or print the report or the like.

BACKGROUND

Conventionally, in a medical setting, various modalities such as an ultrasonic diagnosis apparatus, an X-ray CT apparatus, and an MRI apparatus, have been used. After viewing an image taken by those modalities, doctors produce a report. In producing the report, a medical image that has been acquired in advance is often pasted.

However, conventionally, while the produced report can be printed by a printer or the like, a background of an ultrasonic image or the like is blotted out with black in many cases. Therefore, a problem is that the cost of using ink increases as the produced report is printed. One solution to the problem is a monochrome inversion function.

The monochrome inversion function is to invert a monochrome level of the image pasted in the report, a black image is converted into a white image, and the white image is converted into the black image. However, if all an area of the image is simply subjected to a monochrome inversion process, for example, a color image of the ultrasonic image is inverted too. The inversion of the color image may pose a problem.

In the case of the ultrasonic image, for example, an image of blood flow is displayed as a color image, a flow of blood in a direction away from an ultrasonic probe is displayed in blue hue, and a flow of blood in a direction toward the ultrasonic probe is displayed in red hue. Accordingly, if the monochrome inversion is simply carried out, the color image is inverted too, the blue image is converted into red image, and the red image is converted into blue image. As a result, the colors indicating the blood flows become inverted, disrupting diagnosis.

DETAILED DESCRIPTION

A medical image diagnosis apparatus of an embodiment includes: an image generation unit configured to generate a first image which is an original image, from a medical image taken by a medical imaging unit; an image conversion unit configured to process the first image to output a second image where a color tone of a predetermined region in the first image is kept and a color tone of a region other than the predetermined region is converted; and an image output unit configured to supply the second image to an output apparatus.

Hereinafter, the medical image diagnosis apparatus of the embodiment will be described in detail with reference to the accompanying drawings. Incidentally, in each diagram, same portions are represented by same reference symbols.
(First Embodiment)

Figure 1:
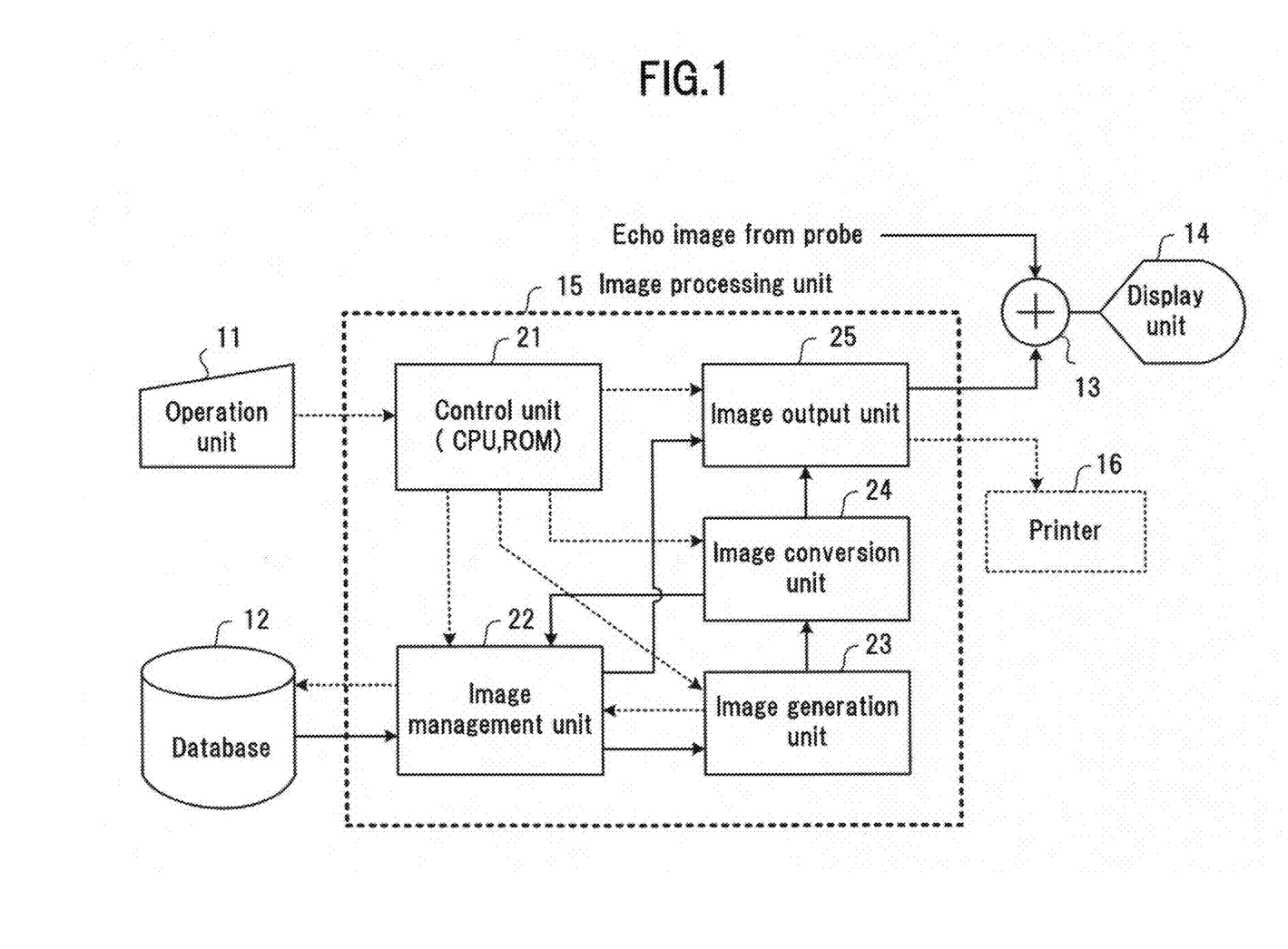
FIG. 1 is a block diagram showing a configuration of a medical image diagnosis apparatus according to one embodiment.

FIG. 1 is a block diagram showing the configuration of the medical image diagnosis apparatus according to one embodiment. The medical image diagnosis apparatus shown in FIG. 1 includes an operation unit 11, a database 12, a synthesis processing unit 13, a display unit 14, and an image processing unit 15. The medical image diagnosis apparatus may also include a printer 16. Incidentally, in FIG. 1, solid arrows indicate information lines, and dotted arrows indicate control lines.

The operation unit 11 is operated by operators such as doctors. The operation unit 11 includes input apparatuses such as a keyboard and a mouse. As the input apparatuses are operated, various instructions (e.g., instructions for selecting an image or converting an image, and user setting information such as instructions for an image conversion region) are input to the image processing unit 15. In the database 12, medical images for diagnosis are stored, the images are taken by various medical imaging unites, such as an ultrasonic diagnosis apparatus, an X-ray CT apparatus, and an MRI apparatus.

The synthesis processing unit 13 outputs an image that an operator creates for a report or the like by using the image processing unit 15 to the display unit 14, or outputs an image from a medical imaging unit (e.g. an echo image sent from a probe in the case of an ultrasonic diagnosis apparatus), or combines two images and then outputs to the display unit 14.

Incidentally, in the embodiment, what is described is a case where a medical image obtained by the ultrasonic diagnosis apparatus is processed. Moreover, an image created by the image processing unit 15 is not only used for the report, but also to be displayed for observation after being stored as a captured image in some cases. The description below focuses on creating an image for the report. Moreover, an image that the operator has created for the report will be simply referred to as the report.

The image processing unit 15 functions as a computer to perform creation of the report or the like. The image processing unit 15 includes a control unit 21, an image management unit 22, an image generation unit 23, an image conversion unit 24, and an image output unit 25.

The control unit 21 includes a CPU (Central Processing Unit) and a ROM (Read Only Memory). In the ROM, an image processing program that the image processing unit 15 uses, and setting data used for producing the report or the like are stored in advance. The CPU controls an operation of the image processing unit 15 and the database 12 in accordance with programs stored in the ROM. The control unit 21 produces the report or the like in response to the operation by the operator of the operation unit 11.

The image management unit 22 manages image data stored in the database 12. The image management unit 22 reads image data from the database 12 and writes image data to the database 12 in accordance with instructions from the control unit 21. Incidentally, suppose that, in the database 12, various medical images taken by the medical imaging unit, e.g. image data of ultrasonic images and the like, are stored in advance. The database 12 is connected to the medical imaging unit such as the ultrasonic diagnosis apparatus, via a network such as LAN. Any image data can be written to and read from the database 12. Accordingly, the database 12 and the image management unit 22 makes up the image acquisition unit that acquires the medical image taken by the medical imaging unit.

The image generation unit 23 processes an image transmitted from the image management unit 22 to generate a first image, for example an original image that can be displayed by the display unit 14. Moreover, the control unit 21 receives user setting information such as preset information from the operation unit 11, and transmits the received user setting information to the image generation unit 23. The user setting information includes information about which image is to be converted, and which portion is to be converted, and how the image is to be converted (e.g. image inversion). The operation of image conversion will be described later. The image generation unit 23 determines whether or not the image conversion is required based on the user setting information and the like, and transmits the first image which is the original image, and the user setting information to the image conversion unit 24.

The image conversion unit 24 converts the image received from the image generation unit 23, and then transmits a second image that resultant of conversion to the image management unit 22. The image output unit 25 supplies image data to the display unit 14. The image conversion unit 24 outputs the second image to the printer 16. The display unit 14 and the printer 16 constitute an output apparatus, and are used to display and print image data from the image output unit 25.

Figure 2A:
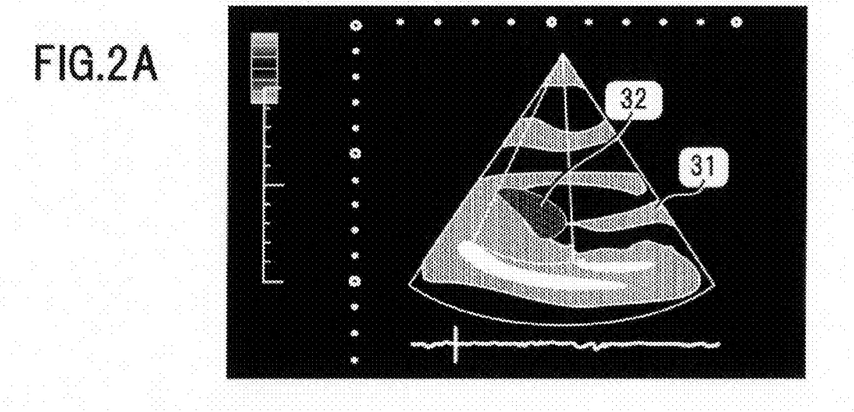
FIGS. 2A, 2B, and 2C are explanatory diagrams showing one example of images converted by an image conversion unit according to one embodiment.
Figure 2B:
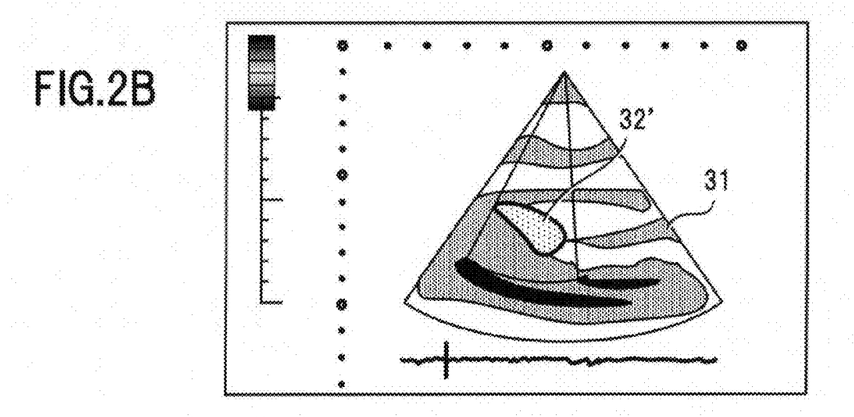
Figure 2C:
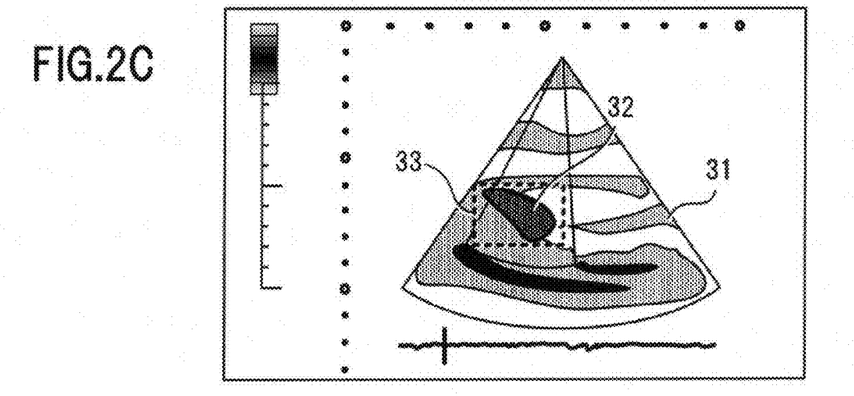

With reference to FIGS. 2A to 2C, the operation of an image conversion process of the embodiment will be described.

First, the operator operates the operation unit 11 to choose a previous image (or an ultrasonic image in this case) that exists in the database 12, and displays the image on the display unit 14 to see the image. After the operator operates in such a way as to start image conversion of that reference image, the control unit 21 instructs the image management unit 22 to read the specified image.

The image management unit 22 reads the specified image from the database 12, and transmits the read image to the image generation unit 23. The image generation unit 23 processes the read image to generate the first image, for example, an image (referred to as an original image) that can be displayed by the display unit 14. Moreover, the control unit 21 transmits the user setting information to the image generation unit 23. The image generation unit 23 makes a determination as to whether or not an image conversion is required. If the image conversion is required, the image generation unit 23 transmits the original image and the user setting information to the image conversion unit 24.

The image conversion unit 24 determines, based on the user setting information, what kind of a conversion process should be performed. The image conversion unit 24 also automatically determines which portion of the image received from the image generation unit 23 should be converted. The image conversion unit 24 generates the second image where a color tone (brightness and color) of the automatically determined portion has been converted, and transmits the converted image to the image management unit 22.

After the converted image is transmitted to the image management unit 22, the control unit 21 instructs the image output unit 25 to output the second image obtained by the conversion, the second image is displayed on the display unit 14, or is printed by the printer 16. The converted image is stored in the database 12 when necessary.

FIGS. 2A to 2C are explanatory diagrams showing an example of displaying images (the second image) that have been converted by the image conversion unit 24. FIG. 2A shows an example of an original image (ultrasonic image 31) generated by the image generation unit 23. FIG. 2B shows an image where all region has been simply inverted as a result of image conversion. Incidentally, the image inversion means a monochrome inversion or a color inversion. In the case of a monochrome image, the inversion of a white image produces a black image, and the inversion of a black image produces a white image, in the case of a color image, the inversion of a blue image produces a red image, i.e. a complementary-color image.

As shown in FIG. 2A, if the background of the ultrasonic image 31 is black, the background of the ultrasonic image 31 becomes white as a result of an image inversion process by the image conversion unit 24, as shown in FIG. 2B, the monochrome images of the ultrasonic image 31 are inverted too. If all area shown in FIG. 2A is simply inverted, even a color image 32 of the ultrasonic image 31 becomes inverted. For example, if the color image 32 is red, the conversion produces a bluish color image 32'. In this manner, the color tone is changed.

However, in the case of the ultrasonic image, for example, an image of blood flow is displayed as a color image, a flow of blood in a direction away from an ultrasonic probe is displayed in blue hue, and the flow of blood in a direction toward the ultrasonic probe is displayed in red hue. Accordingly, if th color inversion is simply carried out, the color image is inverted too, and the color tone is changed. A red image 32 is converted into a blue image 32', and the red image is converted into the blue image. In this manner, the colors indicating the blood flows become inverted. Moreover, in addition to the images indicating the blood flows, there are other images whose meanings might be changed if colors are converted.

According to the embodiment, for example, a color image region is automatically distinguished from a monochrome image region, as shown in FIG. 2C, only the monochrome image is inverted, and the color image is not inverted. As a result, the color image 32 whose original color tone is maintained is output. Alternatively, based on the user setting information, a region where no image is converted may be specified, the color image 32 with an original color tone may be output while the color tone of an image in the specified region is maintained.

For example, as shown in FIG. 2C, a non-conversion region 33 is specified by the operator. In the specified region 33, the image inversion process is not carried out, and the same color tone is maintained. In the other region, the image inversion (monochrome inversion) is carried out. Therefore, the color image 32 having a specific meaning can be displayed in such a way as that the original meaning remains unchanged.

Figure 3:
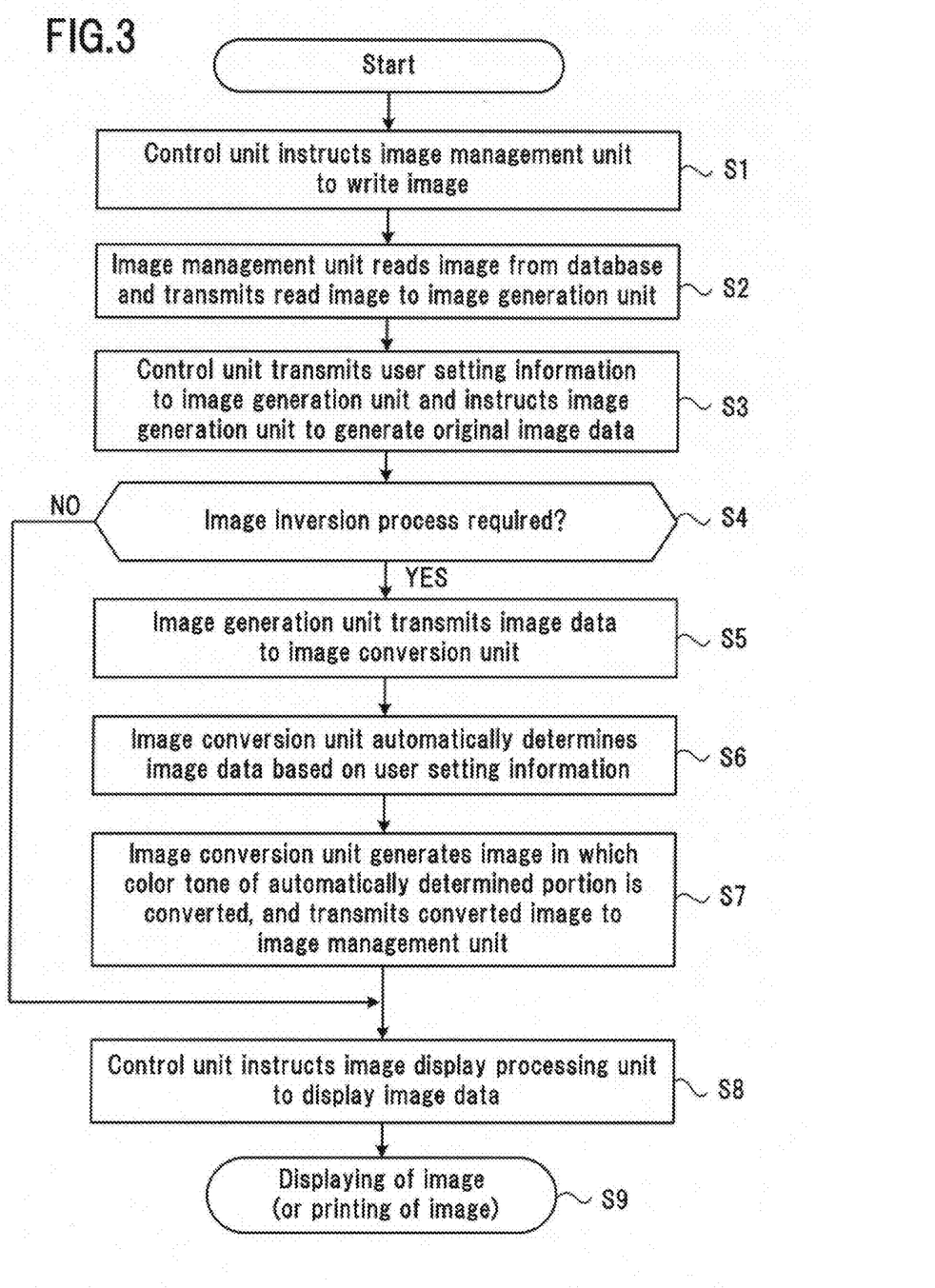
FIG. 3 is a flowchart showing an overall operation of image conversion according to one embodiment.
Figure 4:
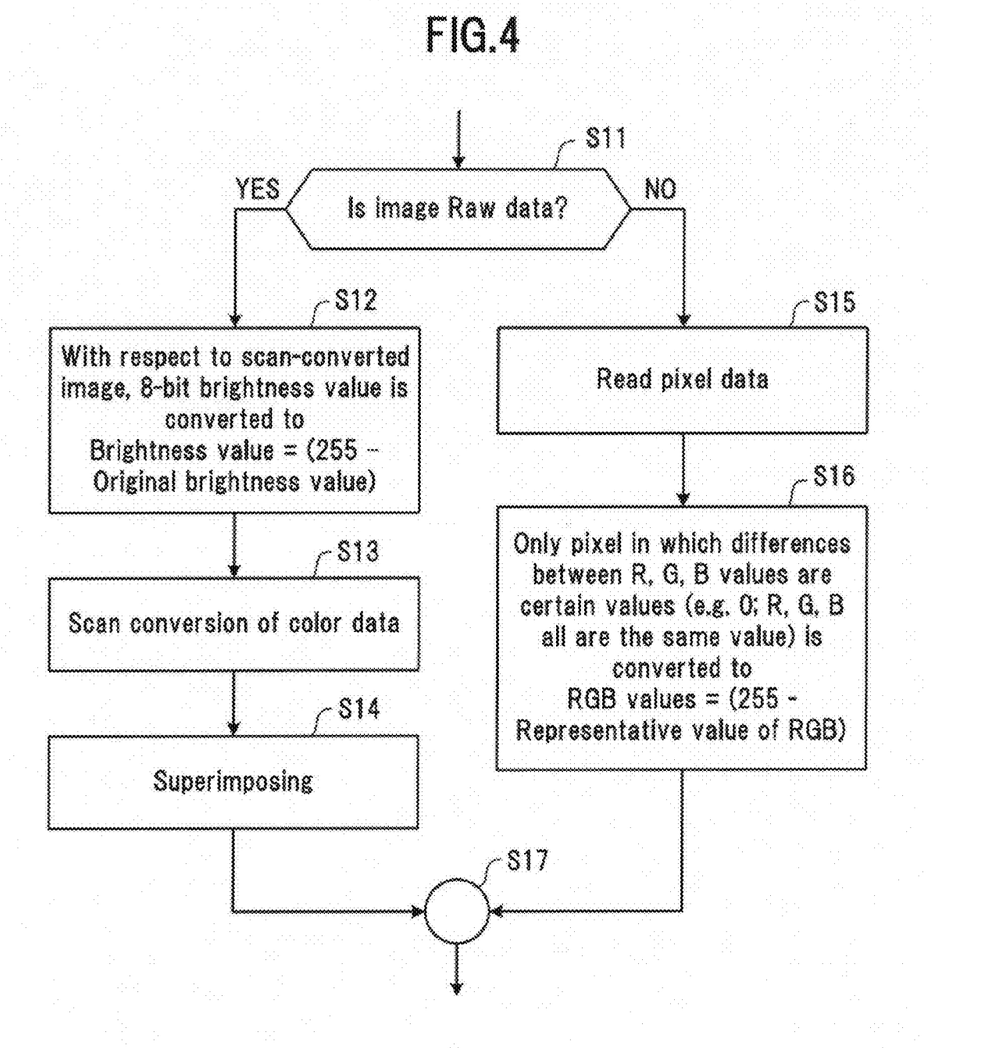
FIG. 4 is a flowchart showing a specific operation of image conversion according to one embodiment.

FIGS. 3 and 4 are flowcharts showing the operation of image conversion in the image conversion unit 24. At step S1 of FIG. 3, the control unit 21 instructs, based on instructions from the operator, the image management unit 22 to read the medical image that exists in the database 12. At the next step S2, the image management unit 22 reads the specified medical image from the database 12, and transmits the read image to the image generation unit 23.

At step S3, the control unit 21 transmits the user setting information to the image generation unit 23, and instructs the image generation unit 23 to generate original image data. At step S4, the control unit 21 determines whether or not the image inversion process is required. If the image inversion is required, the image generation unit 23 at step S5 transmits the original image data to the image conversion unit 24.

At step S6, the image conversion unit 24 automatically determines image data based on the user setting information and the like, the image conversion unit 24 determines which portion of the image data is to be converted, and how the image conversion is to be performed. At step S7, the image conversion unit 24 inverts an automatically determined portion of the image, and transmits the second image obtained by the conversion to the image management unit 22.

If it is determined at step S4 that the image inversion is not required, or after step S7, the process proceeds to step S8. At step S8, the control unit 21 transmits non-inverted image data or inverted image data to the image output unit 25, and instructs the image output unit 25 to display the image data on the display unit 14. Then, after the image is displayed at step S9, the process comes to an end, or after the image data is supplied to the printer 16 and is printed, the process comes to an end.

FIG. 4 is a flowchart showing a specific operation of the image conversion process (image inversion) at step S7. In FIG. 4, at step S11, a determination is made as to whether or not the image is Raw data. If the image is Raw data, the process proceeds to step S12. If the image is not Raw data, the process proceeds to step S15.

Raw data is data before being turned into a picture both monochrome image data and color image data can be retrieved from the Raw data. The monochrome image and the color image are processed separately before being combined. That is, at step S12, for example, with respect to a scan-converted image an eight-bit brightness value is converted to:

Brightness value=(255−Original brightness value)

That is, the bright value is represented by 256 gradations, ranging from 0 to 255. If a white level is a peak value (255), 255−255=0. The white level is therefore converted to a black level. Conversely, if the black level is a minimum value (0), 255−0=255, the black level is therefore converted to the white level. In this manner, the monochrome inversion process is carried out, and the color tone of the monochrome image is changed as a result.

At the next step S13, a scan conversion of color data is carried out. If the control unit 21 gives instructions not to perform the image conversion process on the color image to maintain the color tone, the color image is output without being converted. At step S14, the monochrome image is superimposed on the color image, and the process proceeds to a selection step S17.

If it is determined at step S11 that the image is not Raw data, pixel data is read at step S15. Image data of an image that is not Raw data is for a RGB image obtained by combining a monochrome image and a color image. Therefore, at step S16, only a pixel in which differences between R, G, and B values are within a certain range is inverted and converted to.

RGB values=(255−Representative value of RGB values)

For example, pixels of a white image and a black image have similar R, G, and B values (e.g., 255 or 0). Therefore, the differences between those values (|R−B|, |G−B|, and |R−G|) are very small. Therefore, if the differences between R, G, and B values are within a certain range (e.g., ≠0), one of the R, G, and B values can be used as a representative value, and the image inversion process can be performed by performing the conversion (255−Representative value).

In the case of pixels of the color image, the R, G, B values are different, and the differences therefore are large. Accordingly, if the differences between R, G, and B values are outside the certain range, the image conversion is not performed, and the original image data is just output while the color tone thereof is maintained. At step S17, the image processed at step S14 or S16 is output before the process comes to an end.

Incidentally, in FIGS. 3 and 4, an example of outputting the color image with the color tone thereof maintained is described. However, as shown in FIG. 2C, the color tone of the color image may not be converted only in the region 33 specified by the operator, and the color image may be output. Alternatively, the image conversion may not be performed outside the region specified by the operator, and the image conversion may be performed only inside the specified region. That is, the image conversion unit 24 specifies a region where the image conversion is performed, based on the user setting information, while maintaining the color tone of one image either inside or outside of the specified region and converts the color tone of other image, and to output the second image.

Therefore, according to the first embodiment, the report can be displayed as the operator wishes. Moreover, when the image of the report is printed by the printer 16, a majority of the image is white. Therefore, the amount of ink used can be reduced.

Moreover, the converted image of the report is printed by the printer 16, and is also stored in the database 12. In this case, the content of the image displayed on the display unit 14 is stored as a captured image. A majority of the captured image is white, helping to reduce the capacity of a storage memory.

The converted report image may be used after being converted into PDF (Portable Document Format). If the image is stored in PDF format, a majority of the converted report image is white as shown in FIG. 2C. Therefore, the capacity of a memory used for format conversion can be reduced.

FIGS. 2A to 2C only show one example of the image conversion. Hereinafter, other processing forms of the image conversion will be described.

(Second Embodiment)

According to the second embodiment, images of arbitrary regions are identified, and an image conversion process or a non-conversion process is carried out for each region.

Figure 5A:
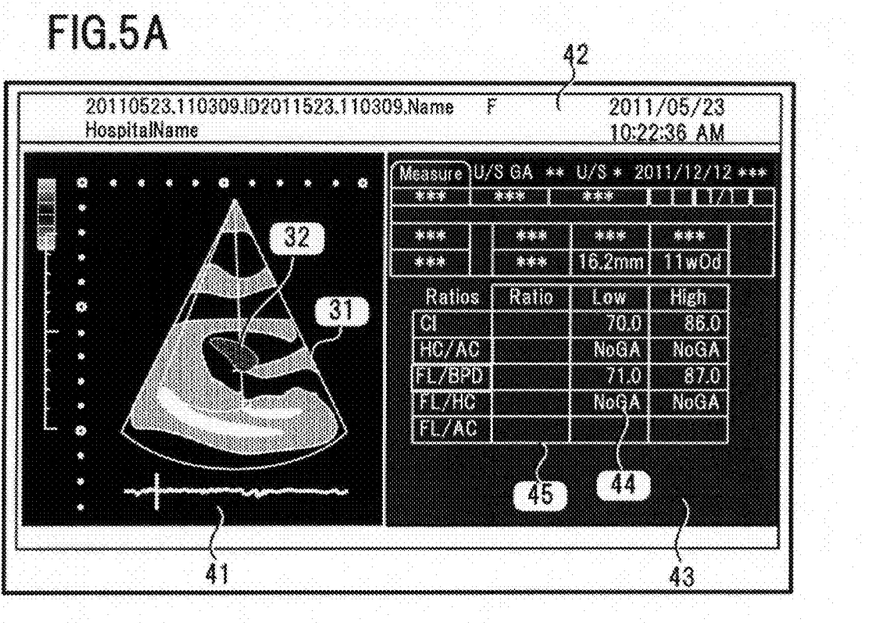
FIGS. 5A and 5B are explanatory diagrams showing one example of images before and after image conversion according to a second embodiment.
Figure 5B:
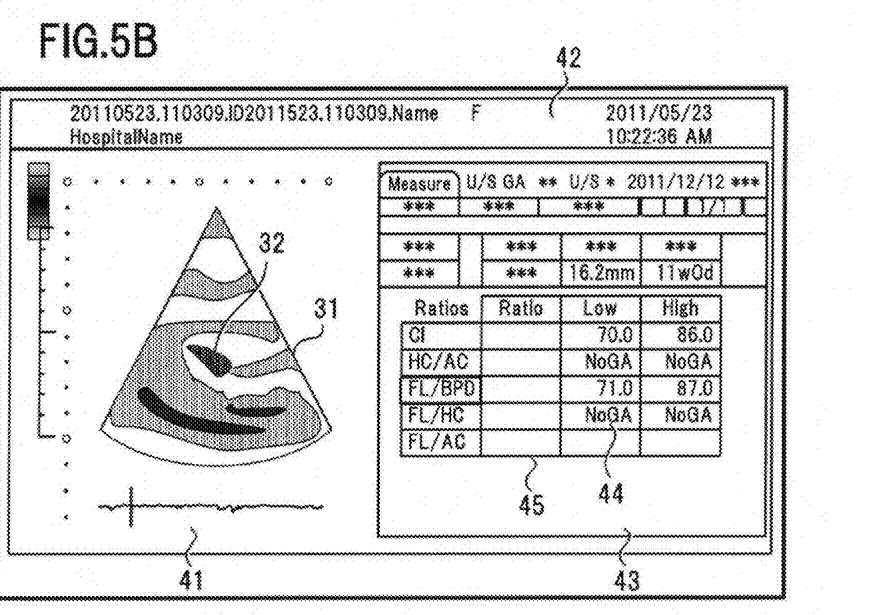

FIGS. 5A and 5B show an example in which an ultrasonic image 31 is pasted in a report, and a worksheet of measurement data 43 and the like is disposed nearby. In the case of FIG. 5A, there are a region 41 that includes the ultrasonic image 31, a region 42 that shows a title of the report, and a region 43 for the measurement data. For example, when images of the region 41 containing the ultrasonic image 31 are to be inverted, a color image is not inverted. Moreover, images of the region 42 that shows the title is not inverted. In the region 43 for the measurement data, images representing characters 44 and lines 45, and an image of the background are converted. Instructions given by operation of the operation unit 11 determine which region's images are to be converted, and which region's images are not to be converted.

FIG. 5B is an explanatory diagram showing an example of image conversion performed on the report of FIG. 5A. In the case of FIG. 5B, in the region 41 containing the ultrasonic image 31, as in the case of FIG. 2C, a monochrome image is inverted, and the color image 32 is not inverted in order to maintain the color tone thereof. Accordingly, the color tone of the color image 32 is maintained, and a background image and a monochrome image of the ultrasonic image 31 are inverted and displayed.

In the region 42 showing the title, images are displayed in accordance with original data, without being converted at all. In the region 43 for the measurement data, a background image becomes a whitish image as a result of monochrome inversion, the characters 44 and the lines 45 are displayed in black as a result of monochrome inversion. Accordingly, the report is displayed as the operator wishes. Moreover, a majority of the report becomes a white image when being printed. The amount of ink used therefore can be reduced.

Moreover, in the case of FIG. 5B, in the region 43 for the measurement data, the color of the background image may be arbitrarily changed as the operator wishes. The image conversion may take place in such a way that the colors of the characters 44 and lines 45 are different from the color of the background. In this manner, the color tone may be changed when being displayed.

Furthermore, while the color tone of the color image 32 having a specific meaning within the ultrasonic image is maintained, the other, arbitrary images may be converted into an arbitrary color. In this case, the produced report can be printed in colors that the operator likes.

(Third Embodiment)

According to a third embodiment, as for color images that have a common meaning among a plurality of images, an image conversion process that has been applied to one image is also applied to the other images.

Figure 6A:
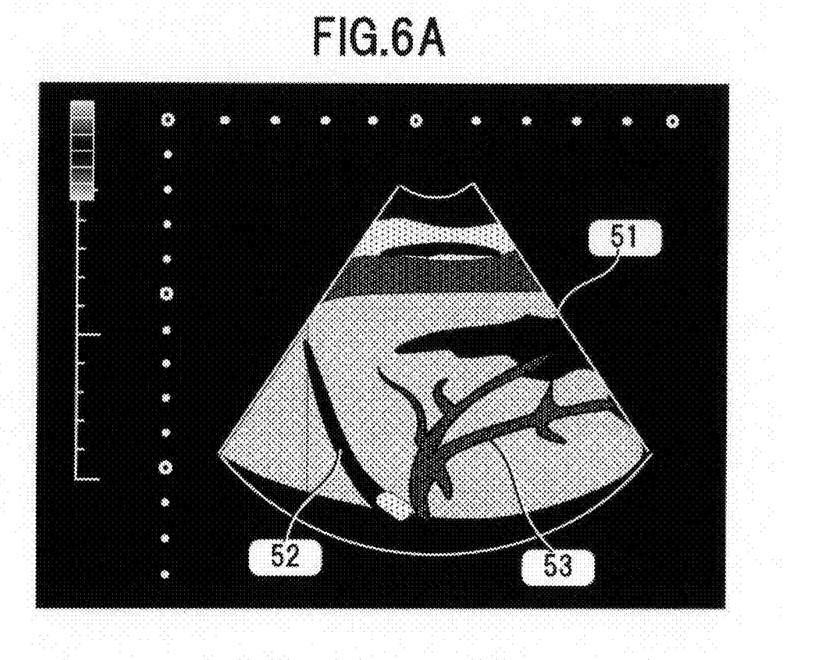
FIGS. 6A and 6B are explanatory diagrams showing one example of images before and after image conversion according to a third embodiment.
Figure 6B:
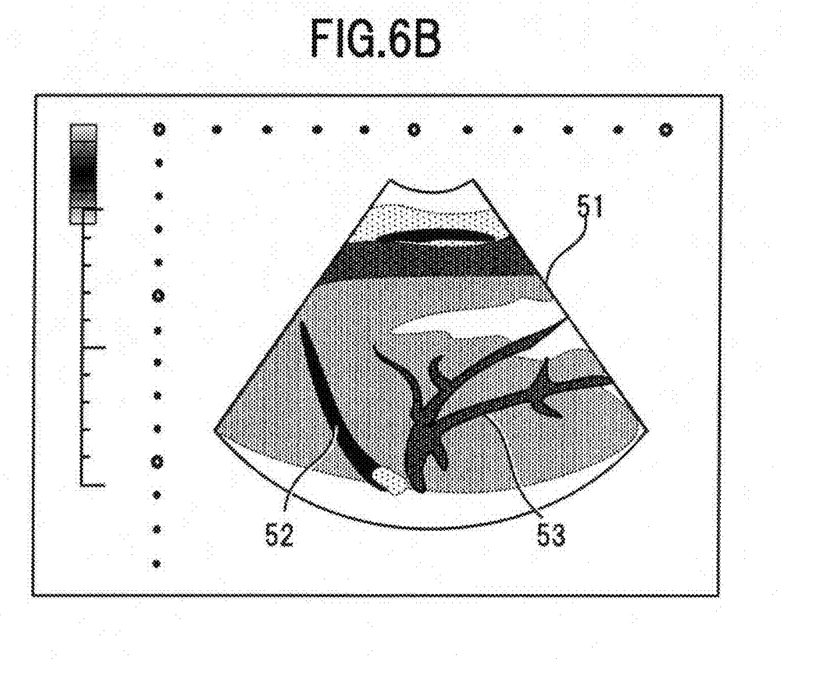

FIGS. 6A and 6B show images where the hardness of an organ in a lesion site is represented by colors, or an ultrasonic image 51 that is used for diagnosis of diffuse disease such as fatty liver. In FIG. 6A, a hard portion 52 of the organ is displayed in blue, and a soft portion 53 is displayed in a warm color (orange). The colors representing the hardness of an organ should have the same meanings in other ultrasonic images to make diagnosis easy. Accordingly, the color images 52 and 53 having the same meanings should not be converted. The original color tone should be maintained when being displayed.

FIG. 6B shows an example in which inverted images of FIG. 6A. In FIG. 6B, the monochrome inversion of a background image and the ultrasonic image 51 is carried out before the images are displayed. However, in the ultrasonic image 51, the color images 52 and 53 having the common meanings among a plurality of images are not inverted and are displayed in the original data's color tone. Alternatively, the entire ultrasonic image 51 that contains the color images 52 and 53 having the common meanings among a plurality of images may not be inverted.

Incidentally, if data of the worksheet as shown in FIGS. 5A and 5B is created adjacent to the ultrasonic image 51, images of the worksheet region may be converted in the same way as in FIG. 5B. Moreover, if the ultrasonic image of another organ is pasted in the report, the same image conversion process as that in FIG. 6B makes diagnosis easier.

Figure 7A:
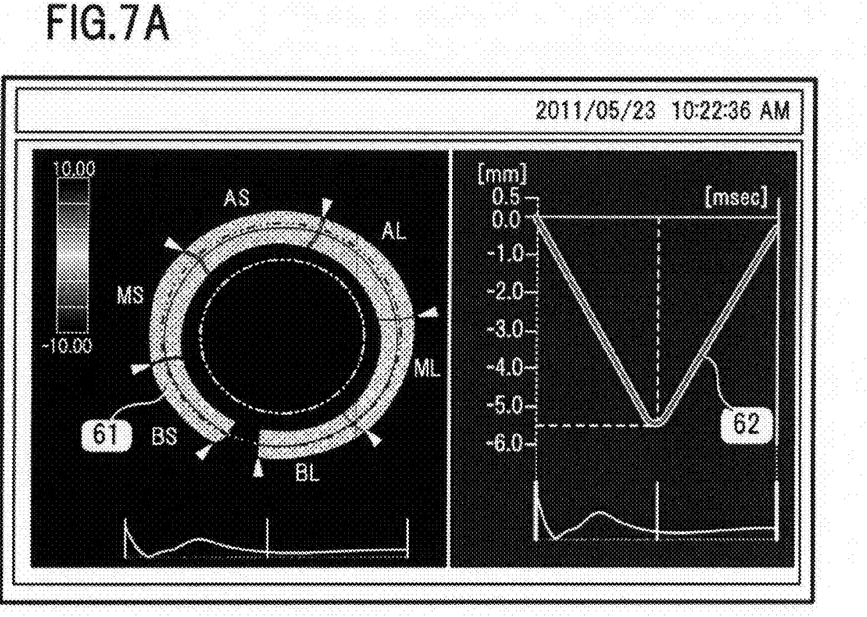
FIGS. 7A and 7B are explanatory diagrams showing another example of images before and after image conversion according to the third embodiment.
Figure 7B:
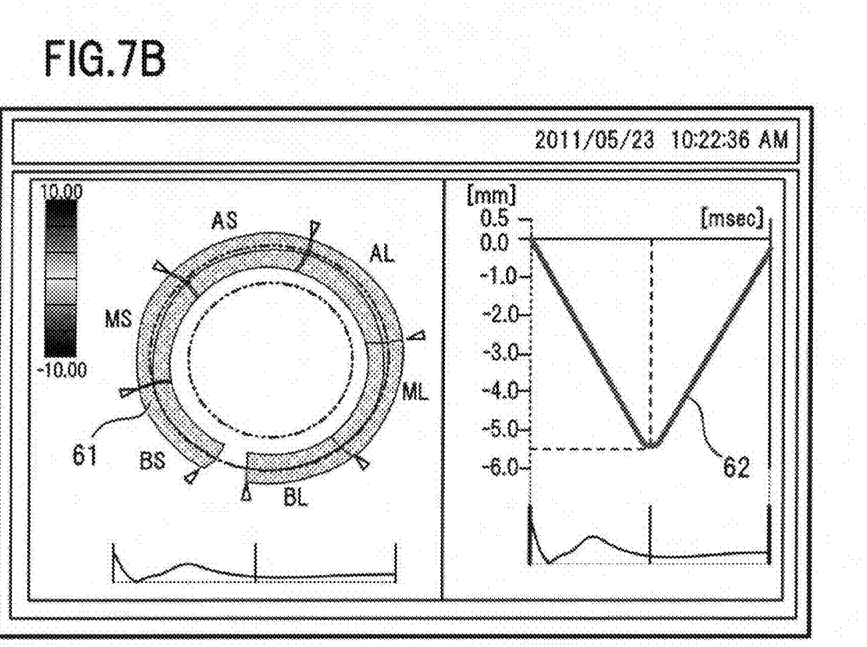

FIGS. 7A and 7B are explanatory diagrams showing an example in which another ultrasonic image is pasted in a report. In order to evaluate motion information of living tissue, the images of FIG. 7A show information 61, which shows wall motions such as displacement or distortion pertaining to a local site in an image, and images including a graph image 62. It is desirable that the wall motion information 61 and the graph image 62 keep the same color tones when being displayed.

FIG. 7B shows an example in which the images of FIG. 7A have been inverted. In FIG. 7B, a background image of the ultrasonic image is displayed as a whitish image as a result of the conversion process. However, the wall motion information 61 and the graph image 62 are displayed in original data's colors as the conversion of the images are not performed. That is, the inversion process has been performed only on the background image, values on the graph, and the like, which are therefore being displayed in different colors.

(Fourth Embodiment)

A fourth embodiment is an explanatory diagram showing a conversion process of images related to a living structure.

Figure 8A:
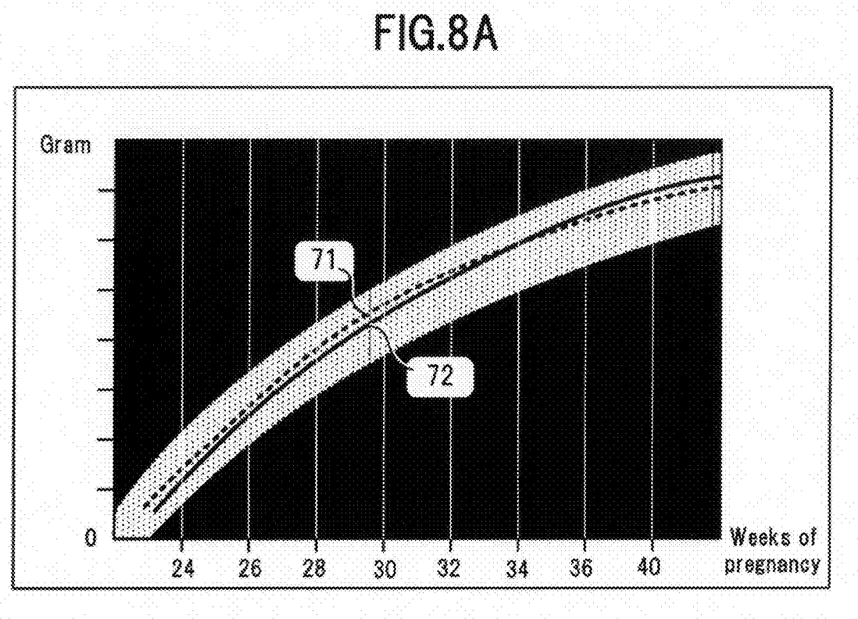
FIGS. 8A and 8B are explanatory diagrams showing one example of images before and after image conversion according to a fourth embodiment.
Figure 8B:
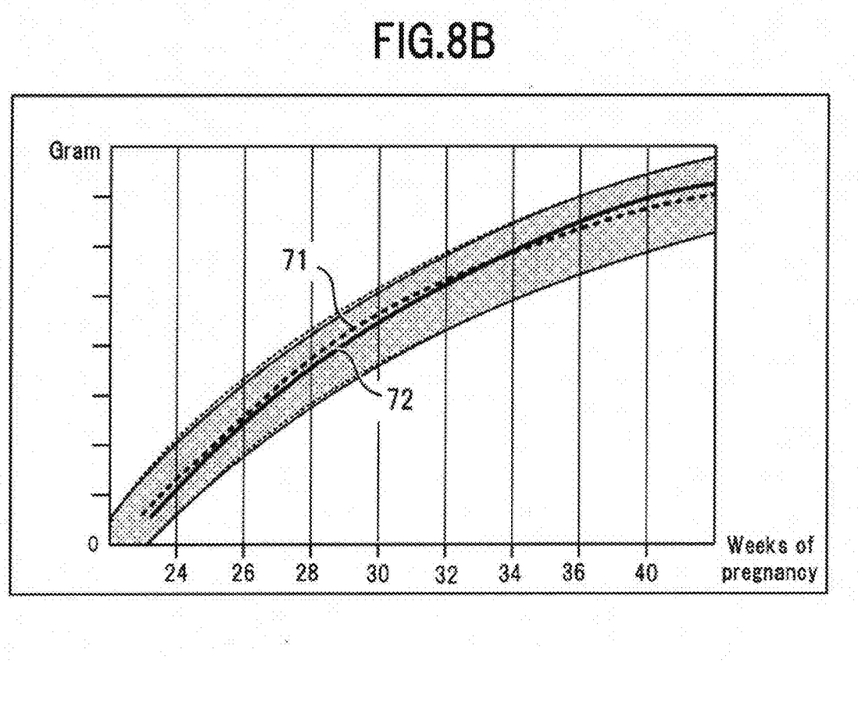

In FIGS. 8A and 8B, what is illustrated is a case where a fetal growth curve (also referred to as a growth curve) is pasted in a report. The fetal growth curve is produced by using a measurement function that the ultrasonic diagnosis apparatus has, and measuring various items (cross-sectional area of the head, estimated weight, and the like), which are indicators of fetal growth.

FIG. 8A shows fetal growth curves 71 and 72 of twins. If the images of the growth curves are just simply inverted, the colors of the growth curves 71 and 72 are changed, making it difficult to distinguish between the twins' fetal growth curves. Therefore, during the image conversion, the colors of the growth curves 71 and 72 are not converted, while the other images such as a background image are converted. FIG. 8B shows an image after the conversion process. FIG. 8B shows an example in which the color tones of the growth curves 71 and 72 are maintained, while the color of the background portion thereof has been converted.

Moreover, one example of displaying an image of a living structure is a case where a fetal face image is displayed. In this case, the fetal face image is not converted and the original image is used; a background image (e.g. black image) of the face image is converted into a white image, helping only the face image stand out when being displayed.

As described above, according to the embodiments, when an operation of producing a report or any other operation is carried out, image data can be inverted by a conversion process specified by the operator. Therefore, when the produced report is printed, an area occupied by a black image can be reduced, resulting in a decrease in the amount of ink used. Moreover, the printed images become easier to view. Moreover, the images displayed on the display unit become easier to view. At a time when the converted images are to be stored or converted into other formats, the capacity of a memory can be reduced.

Furthermore, the color images, and the color images having the common meanings among a plurality of images are not converted, and the original images are displayed. Therefore, it becomes easier to diagnose.

Incidentally, the present invention is not limited to the above embodiments, and may be applied in various other ways. For example, an image that is pasted in a report is not limited to an ultrasonic image, an MRI image, an image obtained by the X-ray CT apparatus, or any other image may be pasted. In accordance with instructions from the operator, a region that is to be inverted may be set for image conversion.

Moreover, the image management unit 22 may hold both an original image and an image obtained by converting the original image. In this case, the image management unit 22 can display the original image instead of the inverted image, or display the original image and the inverted image at the same time. That is, there is a use case where an image not yet inverted is superimposed on the inverted image, and the images are displayed on the display unit 14 to allow the operator to compare the two images. More specifically, in a case where the inverted image is printed out, if the operator feels uncomfortable about how the image has been inverted, then the operator inevitably would feel tempted to check the pre-inversion image. In such a case, both the original image and the converted image, which are held by the image management unit 22, are quickly displayed on the display unit 14 without going through the image conversion unit 24 after the original image is superimposed on the converted image, in order to allow the operator to check.

Furthermore, the image conversion unit 24 may have an automatic conversion function for a process of inverting an original image. The automatic conversion function can reduce the amount of ink used when the created image is printed by the printer 16.

For ease of explanation, the report images illustrated above are enlarged medical images (ultrasonic images and the like). However, when a report is actually produced, the size of an image can be arbitrarily set by the operator. The arrangement of the images and graphs of measured values and the like may be arbitrarily set.

What is described above is an example in which the image processing program is stored in the ROM of the control unit 21. However, a program for executing the image processing may be installed on a computer such as workstation, and be loaded onto a memory. Moreover, a program that causes a computer to execute the image processing may be stored in recording media, such as magnetic disks (hard disks and the like), optical discs (CD-ROMs, DVDs, and the like), and semiconductor memories, for distribution.

While certain embodiments have been described, these embodiments have been presented by way of example only, and are not intended to limit the scope of the invention. Indeed, the novel apparatus and methods described herein may be embodied in a variety of other forms; furthermore, various omissions, substitutions and changes in the form of the apparatus and methods described herein may be made without departing from the spirit of the inventions. The accompanying claims and their equivalents are intended to cover such forms or modifications as would fall within the scope and spirit of the inventions.

What is claimed is:

1. A medical image diagnosis apparatus comprising:
an image generator implemented by circuitry that generates a first image which is an original image, from a medical image taken by a medical imaging apparatus;
an image converter implemented by the circuitry that processes the first image to output a second image where a color tone of a color image region contained in the first image is maintained and a color tone of a monochrome image region is inverted; and
a printer that prints the second image output from the image converter.

2. The apparatus of claim 1, wherein the second image output from the image converter contains an image for a report or an image that is to be stored.

3. The apparatus of claim 1, wherein the image converter recognizes a region of a color image having a specific meaning as a region where the color tone is maintained, if the first image contains the color image having the specific meaning.

4. The apparatus of claim 1, wherein the image converter recognizes a region of an image pertaining to a living structure as a region where the color tone is maintained, if the first image contains the color image pertaining to the living structure.

5. A medical image processing apparatus comprising:
an image generator implemented by circuitry that generates a first image which is an original image, by processing a medical image selected from among a plurality of medical images;
an image converter implemented by the circuitry that processes the first image to output a second image where a color tone of a color image region contained in the first image is maintained and a color tone of a monochrome image region is inverted; and
a printer that prints the second image output from the image converter.

6. The apparatus of claim 5, wherein the second image output from the image converter contains an image for a report or an image that is to be stored.

7. The apparatus of claim 5, wherein the image converter recognizes a region of a color image having a specific meaning as a region where the color tone is maintained, if the first image contains the color image having the specific meaning.

8. The apparatus of claim 5, wherein the image converter recognizes a region of an image pertaining to a living structure as a region where the color tone is maintained, if the first image contains the color image pertaining to the living structure.

9. A medical image processing method comprising:
generating a first image which is an original image using an image generator, by processing a medical image selected from among a plurality of medical images;
processing the first image using an image converter, and outputting a second image where a color tone of a color image region contained in the first image is maintained and a color tone of a monochrome image region is inverted; and
printing the second image outputted from the image converter.

10. The method of claim 9, wherein the second image output from the image converter contains an image for a report or an image that is to be stored.

11. The method of claim 9, wherein the image converter recognizes a region of a color image having a specific meaning as a region where the color tone is maintained, if the first image contains the color image having the specific meaning.

12. The method of claim 9, wherein the image converter recognizes a region of an image pertaining to a living structure as a region where the color tone is maintained, if the first image contains the color image pertaining to the living structure.

* * * * *